United States Patent
Pintal

(10) Patent No.: US 10,049,470 B2
(45) Date of Patent: Aug. 14, 2018

(54) METHOD AND APPARATUS FOR GEOMETRIC CORRECTION OF OCT DATA REPRESENTING A SCAN OBTAINED BY MEANS OF OPTICAL COHERENCE TOMOGRAPHY IMAGING OF A SAMPLE

(71) Applicant: CANON KABUSHIKI KAISHA, Tokyo (JP)

(72) Inventor: Lukasz Pintal, Wleń (PL)

(73) Assignee: Canon Kabushiki Kaisha, Tokyo (JP)

( * ) Notice: Subject to any disclaimer, the term of this patent is extended or adjusted under 35 U.S.C. 154(b) by 380 days.

(21) Appl. No.: 13/953,508

(22) Filed: Jul. 29, 2013

(65) Prior Publication Data
US 2014/0029826 A1 Jan. 30, 2014

(30) Foreign Application Priority Data

Jul. 30, 2012 (EP) ..................................... 12178558

(51) Int. Cl.
| | |
|---|---|
| G06T 11/00 | (2006.01) |
| A61B 5/00 | (2006.01) |
| A61B 3/00 | (2006.01) |
| A61B 3/10 | (2006.01) |
| G01B 9/02 | (2006.01) |
| G01N 21/47 | (2006.01) |

(52) U.S. Cl.
CPC ............ *G06T 11/008* (2013.01); *A61B 3/102* (2013.01); *A61B 5/0066* (2013.01); *A61B 5/7207* (2013.01); *G01B 9/02077* (2013.01); *G01B 9/02091* (2013.01); *G01N 21/4795* (2013.01)

(58) Field of Classification Search
None
See application file for complete search history.

(56) References Cited

U.S. PATENT DOCUMENTS 7,452,077 B2 * 11/2008 Meyer et al. .................. 351/205
8,325,988 B2 * 12/2012 Ren et al. ...................... 382/107
(Continued)

FOREIGN PATENT DOCUMENTS

| EP | 1775545 A2 | 4/2007 |
|---|---|---|
| EP | 1894518 A1 | 3/2008 |

(Continued)

OTHER PUBLICATIONS

Wavemetrics, Curve fitting, Feb. 3, 2010.*

*Primary Examiner* — Sumati Lefkowitz
*Assistant Examiner* — Jiangeng Sun
(74) *Attorney, Agent, or Firm* — Canon USA Inc., IP Division

(57) ABSTRACT

System and method for geometric correction of OCT data representing a scan obtained by means of optical coherence tomography imaging of a sample. First scan morphological data relating to a morphology of the sample in the scan are obtained. Then reference morphological data relating to a reference morphology of the sample are obtained. For each of one or more scans of OCT data scan morphological data are compared with the reference morphological data to determine a relative geometric transformation of the morphology of the scan with respect to the reference morphology. Corrected scan is generated by performing on the OCT data representing the scan a transform that relates to the determined relative geometric transformation.

13 Claims, 5 Drawing Sheets

(56) References Cited

U.S. PATENT DOCUMENTS

| | | | | |
|---|---|---|---|---|
| 8,433,393 | B2* | 4/2013 | Sharma et al. | 600/477 |
| 2011/0267340 | A1* | 11/2011 | Kraus et al. | 345/419 |
| 2012/0140175 | A1* | 6/2012 | Everett | A61B 3/102 |
| | | | | 351/206 |
| 2014/0218363 | A1* | 8/2014 | Dastmalchi et al. | 345/424 |

FOREIGN PATENT DOCUMENTS

| | | |
|---|---|---|
| EP | 2044879 A1 | 4/2009 |
| WO | 2006077107 A1 | 7/2006 |
| WO | WO 2010140476 A1 * 12/2010 | ........... G06T 7/0012 |

\* cited by examiner

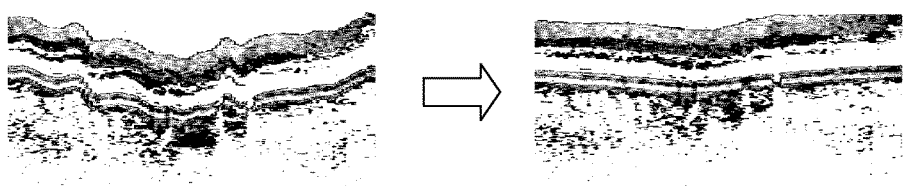
Fig. 1 [Prior Art]
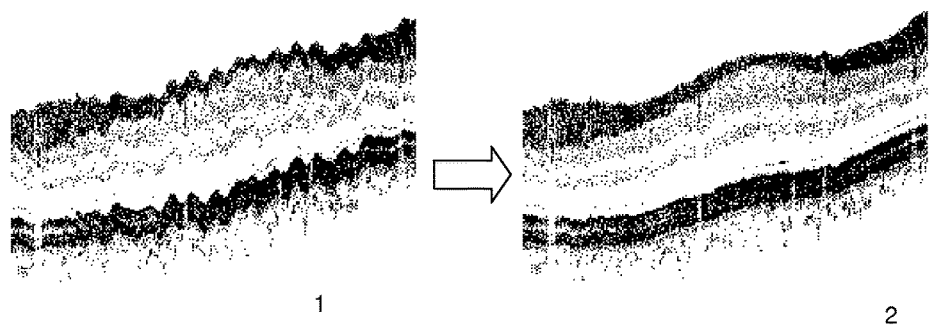
Fig. 2

METHOD AND APPARATUS FOR GEOMETRIC CORRECTION OF OCT DATA REPRESENTING A SCAN OBTAINED BY MEANS OF OPTICAL COHERENCE TOMOGRAPHY IMAGING OF A SAMPLE

CROSS-REFERENCE TO RELATED APPLICATIONS

The present application claims priority under 35 U.S.C. § 119 to European patent application No. EP12178558.8 filed on Jul. 30, 2012 in the European Patent Office. The disclosure of the above application is incorporated herein by reference in its entirety.

BACKGROUND OF THE INVENTION

Field of the Invention

The present invention relates to imaging by optical coherence tomography (OCT). In particular, the invention is directed to correction of errors resulting from a geometric transformation such as displacement of a sample during optical tomography data acquisition, especially OCT scans.

Optical Coherence Tomography is a technique for performing high-resolution cross-sectional imaging that can provide images of tissue structure. OCT is a method of interferometry that determines the scattering profile of a sample along the OCT beam. Each scattering profile is called an axial scan, or A-scan.

An A-scan provides information about the structure of a sample (structural information) in the depth direction of a sample (also called the z-axis or in-depth axis).

A series of A-scans across the surface of the sample permits a cross-sectional reconstruction of a plane through the anterior or posterior segment of The tissue. This is known as a B-scan (also often referred to a tomogram).

A B-scan is formed from a series of A-scans taken along an axis perpendicular to z-axis. Usually those A-scans are taken consecutively. For the sake of clarity this axis (i.e. the direction of collecting consecutive A-scans) that can be literally any axis perpendicular to the in-depth axis hereinafter is denoted as x-axis. Consequently, a B-scan provides structural information of a sample in X-Z plane.

The direction perpendicular to the x- and z-axes is herein denoted as y-axis. Consecutive B-scans may be collected along the y-axis so as to provide a full data set corresponding to a three dimensional (3D) volume or space.

It is clear, that movement of a sample during scanning process causes distortion of the resulting 3D representation of a sample. The distortion is a geometric transformation, typically a mutual shift (displacement), of consecutive B-scans or even A-scans. Movement of the sample is a well known problem in OCT data processing. For example, in case of ophthalmology, a typical patient can comfortably hold his eye open only for a few seconds. OCT systems can advantageously use these few seconds to collect extensive images. During such an acquisition, movement of the patient's eye and natural saccade movements in the patient's fixation will distort the image. Disfigured, misplaced data can be a source of wrong diagnosis. Accordingly, it is very important to devise good methods of correction of such distortions. There are several known methods. U.S. Pat. No. 7,755,769 discloses method based on post processing correction using additional tomograms (B-scans) captured in a y-axis direction, perpendicular to main data tomograms. One disadvantage of this method is the additional time needed for capturing extra data. Other solutions are based on post processing correction only. One solution of this type is implemented in "SOCT Copernicus" device, manufactured by Optopol Technology. In this solution, referring to FIG. 1 of the accompanying drawings, a relative displacement between two consecutive B-scans is found by correlating intensity profiles (averaged A-scans) between the consecutive B-scans. A similar method has been proposed by T. Bajraszewski et al. in "Three-dimensional in vivo imaging by spectral OCT", Coherence Domain Optical Methods and Optical Coherence Tomography in Biomedicine VIII, Proceedings of the SPIE, Volume 5316, pp. 226-232 (2004), DOI: 10.1117/12.529278. Here, the correction of eye's movement along the z-axis is compensated by finding the correlation between consecutive B-scans.

There is therefore a need for a method of correction of an object's geometric transformation (especially displacement in the z-axis direction) in OCT data without additional measurements. Incorrect compensation of displacement of the OCT data may cause errors in further processing of the OCT data (for example tissue boundary detection) and in other calculated parameters. Any errors which occur during medical data analysis may also lead to a wrong diagnosis.

SUMMARY OF THE INVENTION

According to the first aspect of the invention a method for geometric correction of OCT data representing a scan obtained by means of optical coherence tomography imaging of a sample is provided. The method comprises obtaining scan morphological data relating to a morphology of the sample in the scan, and further steps of
  obtaining reference morphological data relating to a reference morphology of the sample;
  for each of one or more scans of OCT data:
    (i) comparing the scan morphological data with the reference morphological data to determine a relative geometric transformation of the morphology of the scan with respect to the reference morphology;
    (ii) generating a corrected scan by performing on the OCT data representing the scan a transform that relates to the determined relative geometric transformation.

Preferably the relative geometric transformation is or includes a displacement.

Advantageously the reference morphological data are obtained from a reference scan other than the scan to be corrected.

Preferably the reference scan and the scan to be corrected are adjacent scans.

Advantageously method is realized in an iterative way. In every iteration, a scan to be corrected and a reference scan are used for determining a relative geometric transformation of the scan morphology with respect of the reference morphology. The reference scan of a current iteration is the scan to be corrected of the preceding iteration.

Preferably the reference scan is selected from among a set of available scans. The reference scan for the first iteration can be selected based on one or a combination of criteria.

Preferably the highest intensity scan is selected as reference scan.

Alternatively the sharpness of the scan may be a criterion for reference scan selection.

Alternatively, the reference scan may be selected on the basis of the morphological data obtained for the scans.

Preferably the reference scan is a center scan among the set of available scans. Then the method is executed in an iterative manner processing subsequent scans in the first direction from the reference one and subsequent scans in the second direction from the reference one.

Preferably, at least one iteration of the processing in the first direction is realized substantially simultaneously (i.e. in parallel) with at least one iteration of the processing in the second direction.

Advantageously the scan morphological data and/or the reference morphological data comprises data representing at least one recognized boundary of at least one specific layer of the sample.

Preferably the scan to be corrected is a B-scan.

Preferably the B-scan extends in an X-Z plane or in an X-Y plane, and the transform performed on the scan to be corrected is or includes a displacement in a displacement in a z-direction.

Advantageously the step of comparing the scan morphological data with the reference morphological data to determine a geometric transformation further comprises the step of calculating a set of said displacements between current B-scan b and reference B-scan r by the formula:

$$\Delta z_{b,c,a} = z_{b,c,a} - z_{r,c,a}$$

where
b denotes B-scan index within a 3D data volume,
a denotes index of A-scans within a single B-scan,
c denotes index of the boundary for which the displacement is calculated, and
$z_{b,c,a}$ is a position along z-axis of c-th boundary for a-th A-scan of b-th B-scan and $z_{r,c,a}$, is a is a position along z-axis of c-th boundary for a-th A-scan of the reference B-scan.

Advantageously when the scan is a B-scan generating a corrected scan involves calculating for the scan to be corrected a single offset value $\Delta z_b$ from the set of displacement values, and applying to the scan to be corrected a displacement equal to or derived from the single offset value $\Delta z_b$.

Preferably single offset value $\Delta z_b$ is calculated by applying formulas:

$$\Delta z_{b,c} = \text{median}(\Delta z_{b,c,a})$$

and $$\Delta z_b = \text{median}(\Delta z_{b,c}).$$

Alternatively that single displacement value $\Delta z_b$ may be calculated as an average of all displacements $\Delta z_{b,c,a}$ corresponding to a given B-scan b.

Advantageously the method includes a further step of applying a curve fitting method to a plurality of such displacement offset values $\Delta z_b$ calculated for different respective scans to be corrected to obtain respective curve fit offset values $\Delta^{qr} z_b$ for those scans to be corrected and applying to those scans to be corrected respective displacements based on the differences between $\Delta z_b$ and $\Delta^{qr} z_b$.

Advantageously a vector of displacement values $\{\Delta z_{b,c,a}\}$ for each A-scan is provided for A-scan by A-scan compensating using layer c of a displacement of said B-scans indexed by b.

Advantageously, the correction is applied twice. Firstly in a first direction and secondly in a second direction orthogonal to the first direction.

Preferably the first direction is x-direction and second direction is z-direction.

Advantageously a reliable data region is defined. Within this region a region of the scan to be corrected the morphological data is expected to be reliable. Data outside said reliable data region are excluded from comparison.

According to another aspect invention provides an apparatus for geometric correction of OCT data representing a scan obtained by means of optical coherence tomography imaging of a sample. The apparatus comprises:
  means for obtaining scan morphological data relating to a morphology of the sample in the scan, and also
  means for obtaining reference morphological data relating to a reference morphology of the sample;
  means for comparing, for each of one or more scans, the scan morphological data with the reference morphological data to determine a relative geometric transformation of the morphology of the scan with respect to the reference morphology; and
  means for generating a corrected scan by performing on the OCT data representing the scan a transform that relates to the determined relative geometric transformation.

According to further aspect the invention provides a program which, when executed by a computer or processor, causes the computer or processor to perform any of the methods described above.

The natural saccade movements of a human eye cause displacements of the retina mainly along xy plane. Such a movement causes distortion of reconstructed 3D structure of the sample and leads to misinterpretation of the results. The 3D data volume can be compensated for object's movement along x-axis direction by using morphological data as well. An algorithm can perform a correlation operation of the morphological data of two adjacent B-scans to find displacement value $\Delta x$ along x-axis. Then B-scans can be displaced in the x-axis direction to compensate for x-axis displacement.

Preferably, the x-axis compensation is performed prior to z-axis compensation.

In a further aspect there is provided 22. A method for geometric correction of one or more tomograms obtained by means of optical coherence tomography imaging of a sample, the method comprising:
  obtaining a plurality of tomograms to be corrected;
  for each of the tomograms to be corrected:
    comparing the tomogram with a reference tomogram to determine a relative geometric transformation of the tomogram with respect to the reference tomogram;
    obtaining a curve fitting value for the tomogram based on relative geometric transformations determined for the tomograms to be corrected;
    generating a corrected tomogram by performing on the tomogram a transform using the determined relative geometric transformation and the curve fitting value.

BRIEF DESCRIPTION OF THE DRAWINGS

FIG. 1, illustrates OCT data representing a cross-section of an eye (perpendicular scan) without (left) and with (right) correction made by conventional method of correcting OCT data based on detection of a RPE-Choroid boundary;

FIG. 2 shows OCT data representing a cross-section of an eye (perpendicular scan) without (1) and with (2) correction using a method according to the invention;

DETAILED DESCRIPTION OF THE PREFERRED EMBODIMENTS

Figure 3:
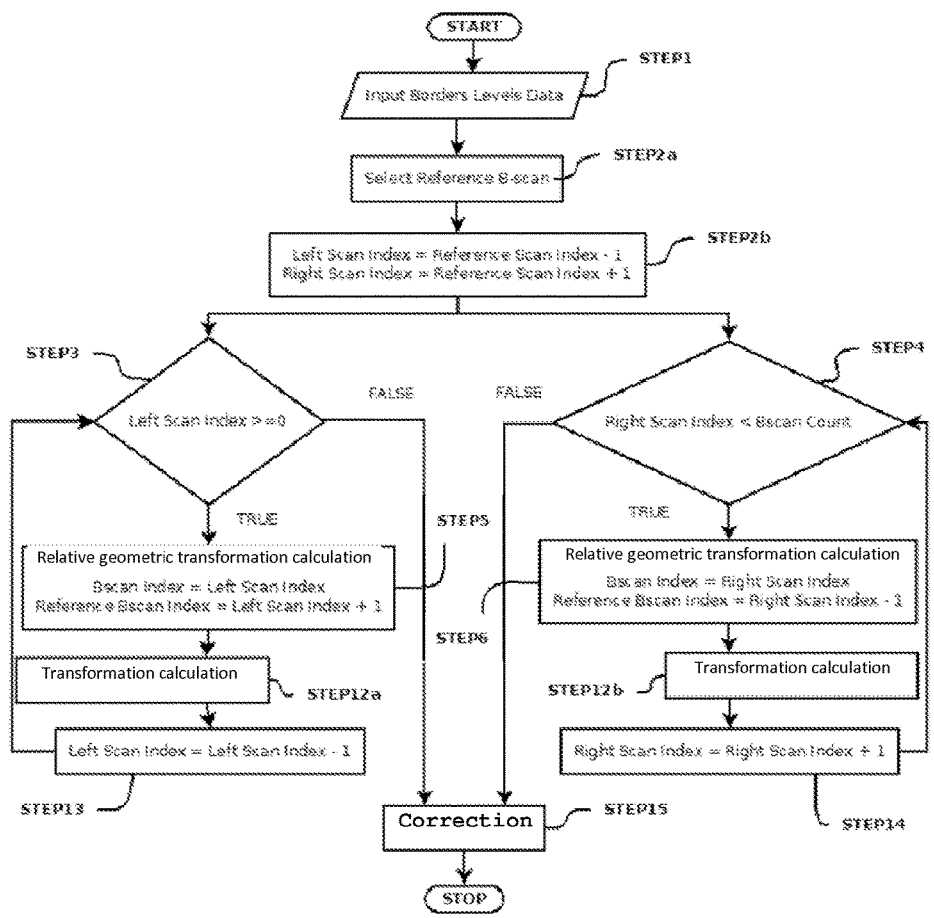
FIG. 3 shows a flowchart for use in explaining a principle of a correction method embodying the invention.

FIG. 3 presents a flowchart of the method according to the invention. The method is explained on an example in which consecutive B-scans are corrected. Nevertheless the same approach may be applied to A-scans, C-scans (corresponding to X-Y planes), or other scans. Input data for the method includes a set of morphological data which in this example represents boundary positions (e.g. X-Z co-ordinates) in OCT tomograms of one or more layers, or segments thereof, of an eye (STEP1). The boundary positions are also referred to as border levels hereinafter. Other kinds of morphological data may be used. For example, edges between abnormalities and normal tissue may be used. Also, when applying methods embodying the present invention to correction of C-scans, the morphological data may relate to features detectable in such scans (X-Y planes), for example an edge between the retina and the surrounding vitreous humor.

Any number of borders between different layers can be detected and used, but the more data is taken into account for calculations, the more robust and precise is the result. Candidate boundaries include Vitreous/RNFL or ILM; RNFL/GCL; GCL/IPL; IPL/INL; INL/OPL; OPL/ONL; ONL/OPL; IS/OS; OS/RPE; RPE/Choroid; Bruch's Membrane (BM), where:

RNFL stands for retinal nerve fiber layer;
ILM stands for Inner Limiting Membrane;
GCL stands for Ganglion Cell Layer;
IPL stands for Inner Plexiform Layer;
INL stands for Inner Nuclear Layer;
OPL—Outer Plexiform Layer;
ONL stands for Outer Nuclear Layer;
IS stands for photoreceptor Inner Segments;
OS stands for photoreceptor Outer Segments; and
RPE stands for Retinal Pigment Epithelium.

There are a number of methods for morphology analysis applicable to images, often referred to as image segmentation (Shapiro, Linda and Stockman, George. "Computer Vision", Prentice-Hall, Inc. 2001). The one particularly applicable herein is for detecting boundaries is to apply an edge detection method to find the best candidates for borders. Only the strongest edges may then be selected, for example edges exceeding a threshold may be selected as corresponding to retina boundaries. Depending on a number of those strongest edges and their order from top of the tomogram to the bottom, it is possible to classify a detected edge as one of the boundaries. Horizontal edge detection filters may be usefully be applied to detect eye layers which are approximately horizontal in a B-scan (X-Z plane). In this case response of the horizontal edge detection filter depends on particular border's characteristic (down from the highest brightness or in an opposite direction).

After obtaining borders levels data, in the next step (STEP2a) reference morphology data is obtained. It relates to a reference B-scan that is selected from among a set of B-scans. Those data constitute the base for left and right directional offsets calculations. The reference scan is conveniently identified by its index r within the set of scans.

In this example, the centre B-scan is selected as the reference B-scan. However, numerous other criteria such as intensity or sharpness can also be applied, either individually or in combination.

After selection of the reference B-scan, processing of subsequent B-scans arranged one after the other along y-axis is applied. The processing is branched into two directions with respect to the reference B-scan. A left direction processing is carried out iteratively using STEP3, STEP5, STEP12a and STEP13 while a right direction processing is carried out iteratively using STEP4, STEP6, STEP12b and STEP14.

In this example, the right direction processing is carried out in parallel with the left direction to improve speed and reduce computing time. However, this is not essential and the left direction processing and the right direction processing can be carried out sequentially instead.

Relative geometric transformations are calculated for left and right side, respectively in the left and right direction processes, starting from the reference (centre in this embodiment) B-scan.

Before starting the left and right direction processes an index used by each processing is initialized in STEP2b. In this step initial values of indices Left Scan Index and Right Scan Index are set to Reference Scan Index minus/plus 1 respectively. These indices are used in the processing to identify a current scan being processed. In a first step (STEP3) of the left direction processing it is checked whether that processing should be terminated. The left direction processing is continued while the left scan index is greater than or equal than 0. STEP4 initiates the right direction processing it is checked whether that processing should be terminated. The right direction processing is continued while the right scan index is smaller than a B-scan count (STEP4), which represents a total number of B-scans available.

The second step is common to both the left and right direction processes and involves current B-scan relative geometric transformation calculations for every analyzed layer border (STEP5 in the case of the left direction process, STEP6 in the case of the right direction process).

In STEP5 a number of relative geometric transformations between current B-scan and reference B-scan is calculated. The number is preferably more than one but it is also possible to calculate just one relative geometric transformation. If more than one is calculated then each relative geometric transformation calculated in this step corresponds to a different subset of morphological data. For example, in the case of a B-scan each subset of the morphological data may correspond to a different layer boundary of the eye. Thereafter an index B-scan Index, representing the index of the current (or target) B-scan, is set to the value of Left Scan Index. Also, another index Reference Bscan Index is set to the value of Left Scan Index+1.

In the first iteration of the left direction processing the left scan index is equal to the Reference Scan Index−1, which means that Bscan Index=Reference Scan Index−1 and Reference Bscan Index=Reference Scan Index. In other words, the target B-scan in the first iteration is the B-scan immediately to the left of the reference B-scan selected in STEP2 and the reference B-scan in the first iteration is the B-scan selected in STEP2.

STEP6 analogous to STEP3 except that its index Bscan Index, representing the index of the current (or target) B-scan, is set equal to the right scan index. Also, its other index Reference Bscan Index is set equal to the right scan index−1. In the first iteration of the right direction processing the right scan index is equal to the Reference Scan Index+1, which means that Bscan Index=Reference Scan Index+1 and Reference Bscan Index=Reference Scan Index. In other words, the target B-scan in the first iteration is the first B-scan to the right of the reference B-scan selected in STEP2 and the reference B-scan in the first iteration is the B-scan selected in STEP2.

In the case in which two or more relative geometric transformations between the current B-scan and the reference B-scan are calculated in STEP5 (or in STEP6) then the set of relative geometric transformations outputted in STEP5 (or in STEP6) is used to calculate a single (overall) geometric transformation for the current B-scan. This is done in STEP12*a* in the left direction processing and in STEP12*b* in the right direction processing. The calculation of single geometric transformation from the number of relative geometric transformations may involve a number of mathematical operations such as determining an average or median value among the set of different relative geometric transformations.

In STEP12*a* and STEP12*b* this resulting overall geometric transformation for the current B-scan is stored for later use. Preferably, prior to storage, the geometric transformation for the current B-scan is superposed on the geometric transformation calculated for the reference B-scan in the present iteration. As a result, the stored relative geometric transformation corresponds to the geometric displacement of the current B-scan relative to the reference B-scan selected in STEP2.

Left and right direction processing are independent. In each step two consecutive tomograms are analyzed. Current B-scan becomes a reference B-scan in following step and its follower becomes new current B-scan.

Then the left scan index used by the left direction processing is decremented by 1 in STEP13 which corresponds to the movement to the left along y-axis. The right scan index used by the right direction processing is incremented by 1 in STEP14, which corresponds to the movement to the right along y-axis.

The next iteration starts in each of the left and right direction processes. In this iteration the target B-scan from the last iteration is used as the reference B-scan, and the target B-scan is the B-scan to the immediate left (in the case of the left direction process) or to the immediate right (in the case of the right direction process) of the reference B-scan.

Once the left and right direction processes have finished, calculated relative geometric transformations are used for perpendicular, circular and radial modifications of tomograms and for correction of boundaries positions for those tomograms. The corrections are done in STEP15.

A simple approach for realization of STEP15 is to iterate through the OCT data correcting it B-scan by B-scan by applying a counter transformation to the transformation calculated in steps 12*a*, 12*b*. The result of such transformation is a flattened image resembling the one presented in FIG. 1. In such situation it is possible to realize correction in steps 12*a* and 12*b* and use corrected B-scans as reference B-scans for subsequent iterations.

Nevertheless it is often preferable to represent OCT data as a shape that resembles the shape of the original object. In such a situation it is preferable to use the set of geometric transformations calculated for all B-scans analyzed in the left and right direction processing and apply to this set a further processing capable of preserving general tendencies in the shape. One suitable type of further processing is to apply curve fitting to the set of geometric transformation values and using values obtained from the calculated curve to determine the transforms to be applied to the OCT data representing the scans to be corrected. This enables obtaining corrected OCT data resembling more closely the original shape of the object.

Figure 4:
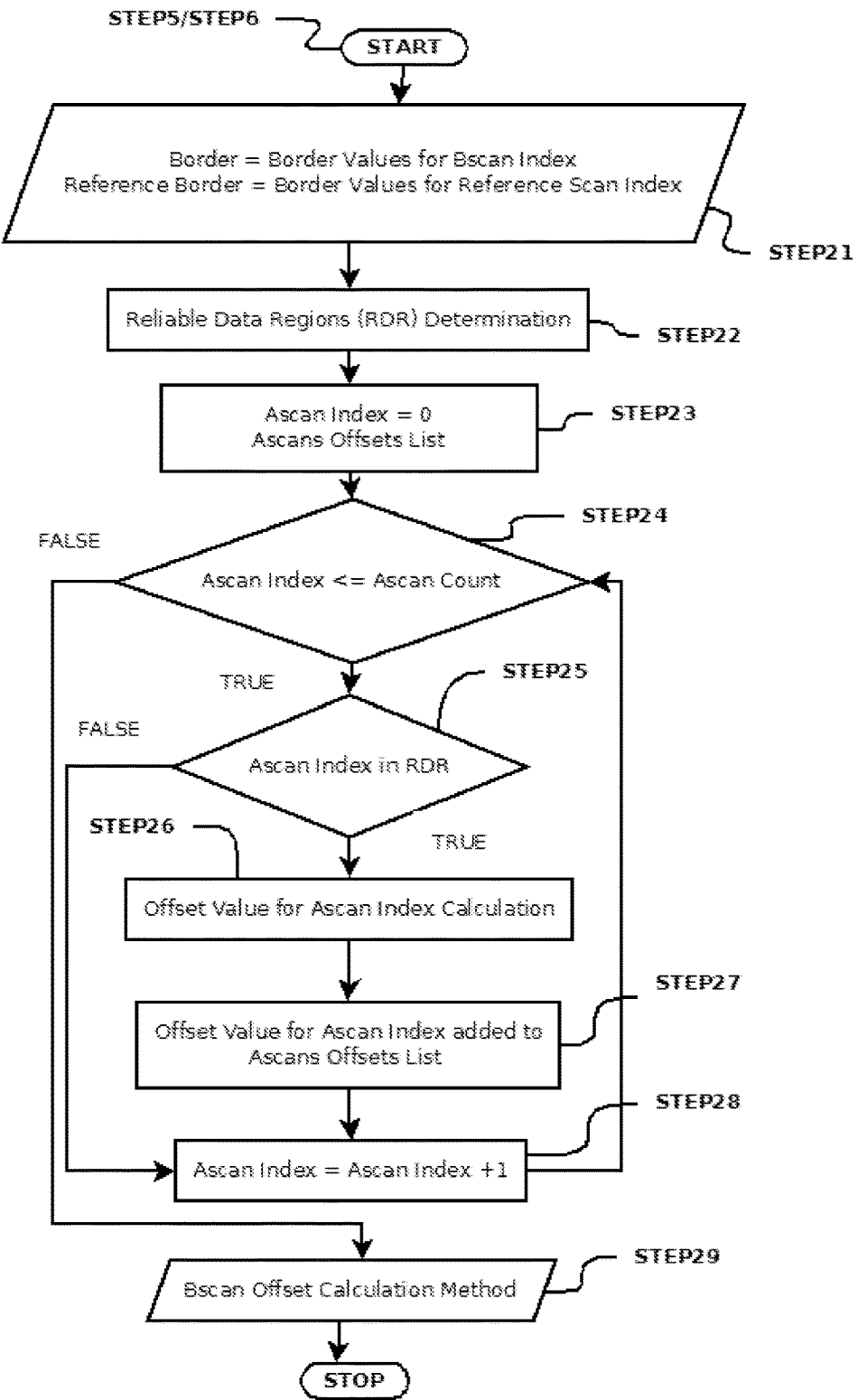
FIG. 4 shows a flowchart presenting in more detail a B-scan offset calculation step in the method of FIG. 3.

An exemplary implementation of STEP5/STEP6 is presented in FIG. 4. In this example relative geometric transformation is limited to a offset along z-axis. It involves a number of sub-steps. Firstly, in STEP21, positions of one or more boundaries detected in the reference B-scan in the current iteration ("Reference Border") are received, and positions of the same boundary or boundaries in the target B-scan as identified by the index Bscan Index are also received.

The next step is to determine scopes of Reliable Data Regions (RDRs) inside which analysis will be performed (STEP22). Boundaries detected outside the RDRs are considered unreliable and are not analyzed. An index, referred to as the Ascan Index, is initialized to 0 and an Ascan Offsets List is emptied (STEP23). The index is used to step one by one through the A-scans in the target B-scan. The Ascan Offsets List is used to gather together displacement information (offset values) for plural A-scans in the target B-scan.

It is then tested whether Ascan Index is less than or equal to Ascan Count which represents the total number of A-scans in the target B-scan (STEP24). If not, all A-scans in the target B-scan have been processed and processing skips to STEP29.

If Ascan Index is less than or equal to A-scan Count in STEP24, next it is checked whether the A-scan with index equal to Ascan Index is inside the determined scope (STEP25), and if so displacement information is calculated (STEP26). The displacement information for each A-scan represents an offset value, that is the relative displacement between the boundaries in the A-scan of the target B-scan and the same boundaries in the corresponding A-scan of the reference B-scan of the current iteration. The displacement information for the current A-scan is added to Ascan Offsets List (STEP27). As a result, displacement information for all A-scans inside the scope of the RDR is gathered into one lit (or matrix), which is expressed by $$\Delta z_{b,c,a} = z_{b,c,a} - z_{r,c,a}$$

where
b—denotes Bscan Index;
a—denotes Ascan Index;
c—denotes Border which stands for the index of boundary for which the displacement is calculated, and
z—is a boundary co-ordinate along z-axis.

The index Ascan Index is incremented by one in STEP28 and the processing returns to STEP24 for the start of the next iteration.

Once the offset values have been gathered for all A-scans within the RDR scope, one B-scan offset value is calculated from the matrix of data for all A-scans inside the RDR scope (STEP29).

Applying the flow chart presented in FIG. 4 to all borders c to be analyzed gives in result a set (or vector) $\Delta z_{b,c}$ of the offsets of the current (b-th) B-scan. One offset corresponds to one border (one subset of the morphological data). Further processing of $\Delta z_{b,c}$ according to the flow chart of the method presented in FIG. 3, involves calculation of single offset value $\Delta z_b$ for the current (b-th) B-scan which corresponds to the geometric transformation indicated in STEP12*a* or STEP12*b*.

A preferred embodiment of the method according to the invention is described with reference to FIGS. 5 and 6. The geometric transformation analysis is therein limited to the displacement along Z-axis direction. The number of analyzed borders is limited to 3 selected from the list given above. Therefore, the layer index $c \in \{1,2,3\}$. In the following description, steps which correspond to those already described with reference to FIGS. 3 and 4 have the same reference numerals and are described only when details differ from or exceed those already described.

(STEP1) Boundaries used for analysis are Vitreous-RNFL, IS-OS and RPE-Choroid (those are the most visible or readily machine detectable boundaries in the tomogram image). The number of boundaries used for calculation of the B-scan offset value may be chosen arbitrarily and is limited only by the boundary detection method used.

(STEP2) The reference scan index is set to B-scan count/2 (central part of scanning area is usually clearly visible). In an alternative embodiment the B-scan with the best quality may be taken as the reference B-scan instead of central B-scan.

(STEP5) This step comprises 4 sub-steps STEP5a, STEP5b, STEP5c and STEP5d. STEP5a uses the Vitreous-RNFL boundary to calculate a first offset value Bscan Offset 1. STEP5b uses the IS-OS boundary to calculate a second offset value Bscan Offset 2. STEP5c uses the RPE-Choroid boundary to calculate a third offset value Bscan Offset 3. STEP5d will be described later. These sub-steps belong to the left direction processing and concern only B-scans to the left of the reference B-scan selected in STEP2.

(STEP6) This step also comprises 4 sub-steps STEP6a, STEP6b, STEP6c and STEP6d, similar to the 4 sub-steps of STEP5. These sub-steps STEP6a, STEP6b, STEP6c and STEP6d belong to the right direction processing and concern only B-scans to the right of the reference B-scan selected in STEP2.

(STEP22) The Reliable Data Regions are used to limit the scope of the analysis. For an individual tomogram (B-scan) the RDR can be defined by border quality markers (the RDR then being the region between the quality markers), disc markers (the RDR then excluding the region inside the disc markers), or by fovea position (the RDR then excluding data inside a 1 mm circle with center within a fovea center). Each iteration of the left or right direction processing has a reference B-scan and a target B-scan (the B-scan immediately to the left or to the right of the reference B-scan). The RDR in the target B-scan may not coincide exactly with the RDR in the reference B-scan. In that case, the RDR of either the target B-scan or the reference B-scan may be selected as a common RDR. Alternatively the common RDR may be defined as the region where the respective RDRs of both B-scans coincide or as the region encompassing both RDRs. In this way, the analysis scope of a given iteration is common for the reference and target B-scans.

Alternatively, RDR can be set constant for all B-scan, e.g. in a vicinity of centre of B-scan, based on an assumption that signals from an object at a central portion of the B-scans (tomograms) always have good quality.

In another alternative embodiment, RDR range can be set constant while RDR position/centre can vary based on analyzed signal of the object under examination. In such a case the fixed range of RDR should be set enough wide to ensure some common portion of RDR for all analyzed B-scans.

(STEP25) In the present embodiment every A-scan within the RDR is processed. However, it is not necessary to processing every single A-scan to obtain satisfactory results. Optionally some A-scans within the RDR are skipped to increase algorithm performance. Effectively, this amounts to sampling the data with some step.

(STEP26) A Z-axis offset value for the current A-scan is defined as the difference, in the z-axis direction, between the border co-ordinate for the relevant border (e.g. Vitreous-RNFL in STEP5a/6a) in the current A-scan in the target B-scan and the border co-ordinate of the same border in the same A-scan in the reference B-scan. For a given border (e.g. vitreous/RNFL) there is a single co-ordinate along z-axis (A-scan).

(STEP29) In the present embodiment, STEP29 comprises sub-steps STEP29a and STEP29b. In STEP29a the list of offset values obtained for all the A-scans in the RDR is sorted in ascending order. Then, in STEP29b, the center Ascan offset value from the sorted Ascans Offset List is selected. That value corresponds to the index Ascans Offset List Count/2. This offset value is the median value among the offset values gathered in the list. In an alternative embodiment an average of the offset values in the list can be used instead.

(STEP12) Returning to FIG. 5, the result Bscan Offset 1 is obtained in STEP5a (STEP6a), the result Bscan Offset 2 is obtained in STEP5b (STEP6b) while the result Bscan Offset 3 is obtained in STEP5c (STEP6c). These offsets correspond to the relative geometric transformation. The median value among these offsets is calculated in STEP5d (STEP6d) and selected as a single overall offset value (Bscan Offset) for the target B-scan (this corresponds to the relative geometric transformation). That value is added to Reference Bscan Offset and then stored. Here, Reference Bscan Offset is the BscanOffset calculated for the Reference Bscan in the present iteration, i.e. the Bscan that has been processed in the previous iteration. In an alternative embodiment an average may be applied instead of median in STEP5d (or STEP6d).

STEP15 when Bscan Offsets $\Delta z_b$ are collected for all analyzed B-scans, then they are processed together as a set (or vector), to preserve the general displacement tendency corresponding to the actual shape of the object. The shape of the object is modeled as a curve, preferably parabola. The vector of Bscan Offsets $\Delta z_b$ corresponds to the samples of the curve at points indexed by b. Index b corresponds to the location of the b-th B-scan in Y-axis direction. Therefore the curve is located in the YZ plane. In STEP15a typical curve fitting techniques are applied so as to determine the values of a parabola best fitting to the points contained in vector $\Delta z_b$. Such techniques are well described in the literature, for example in Handbook of nonlinear regression models by David A Ratkowsky, New York 1990. Herein, a quadratic regression is applied. It is described in The Data Analysis Handbook by Ildiko E. Frank, Roberto Todeschini, Elsevier, 1994 incorporated herein by reference. Quadratic regression applied to $\Delta z_b$ returns a vector Bscan Quadratic Regression Values $\Delta^{qr} z_b$.

After STEP15a a loop starts which goes through the B-scans sequentially starting from the first B-scan (having Bscan index value 0). In STEP15b within the loop the Bscan Quadratic Regression Value $\Delta^{qr} z_b$ calculated for the current B-scan is subtracted from the stored Bscan Offset for the current B-scan to obtain a difference $\Delta' z_b$:

$$\Delta' z_b = \Delta z_b - \Delta^{qr} z_b$$

Finally each B-scan is corrected using the difference $\Delta' z_b$. Effectively, the B-scan is counter displaced i.e. shifted by a value "$-\Delta' z_b$". Thanks to such manner of calculation of the correction values, the corrected OCT data resembles the example presented in FIG. 2 as opposed to the flat example presented in FIG. 1.

Figure 5:
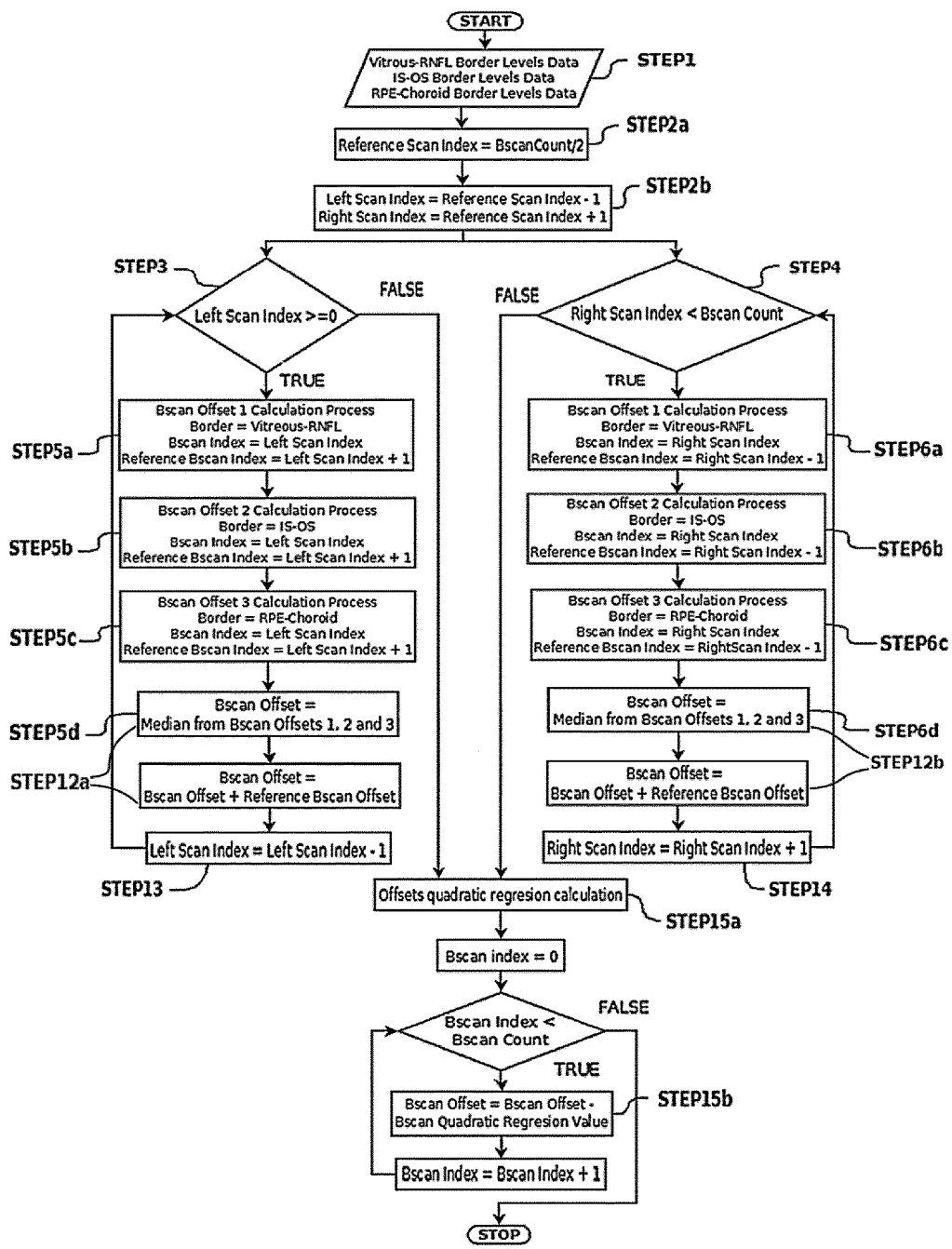
FIG. 5 shows a flowchart for use in explaining a preferred embodiment of the method according to the invention.
Figure 6:
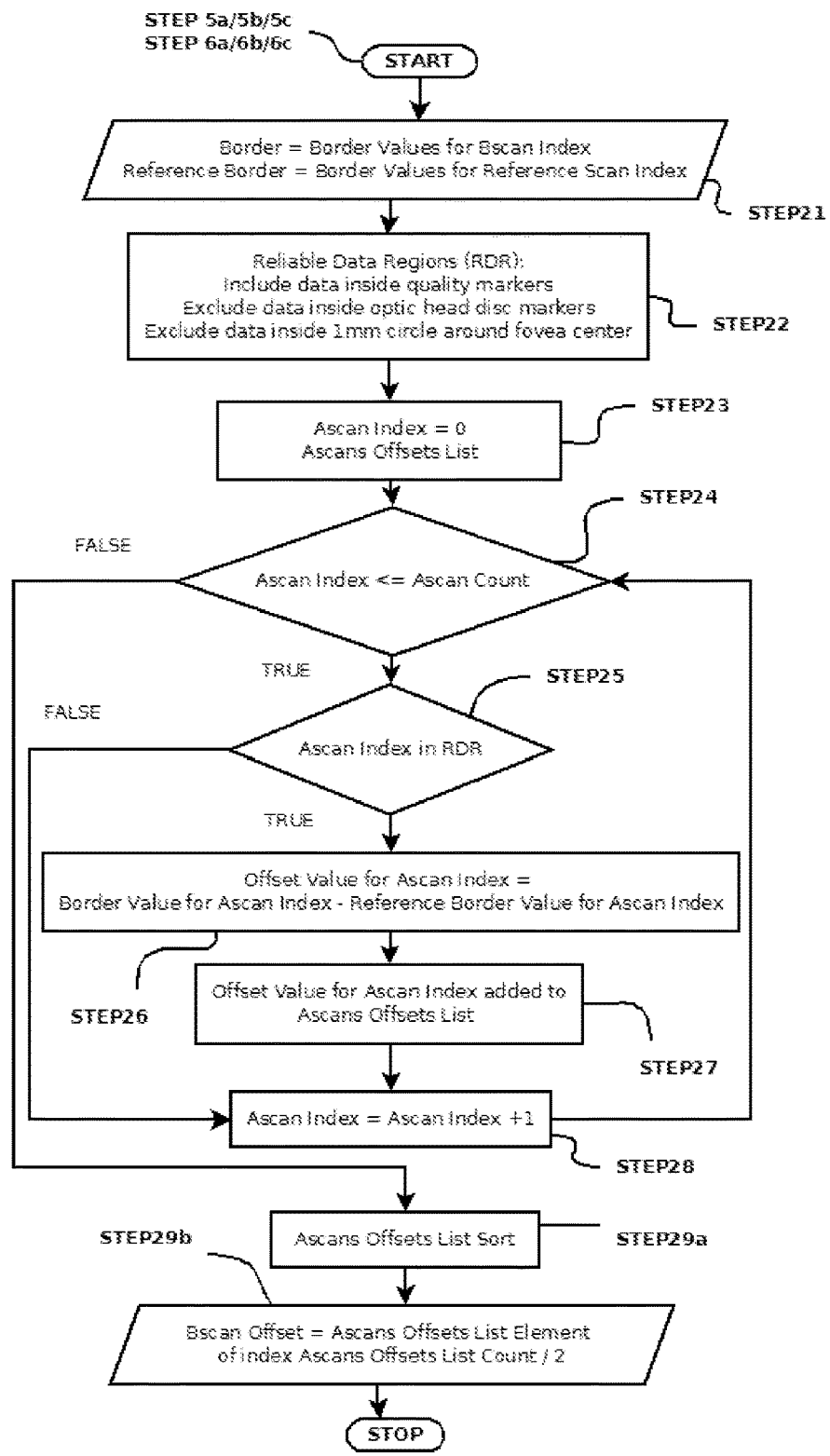
FIG. 6 shows a flowchart presenting in more detail than FIG. 5 a B-scan offset calculation step in the method of FIG. 5.

It is worth noticing that applying a method presented in flowcharts of FIGS. 5 and 6 is basically equivalent to obtaining a vector $\Delta z_b$ by determining offsets for all analyzed A-scans (ie. all A-scans for all B-scans) and for all analyzed borders. Such offsets form a three dimensional matrix $\Delta z_{b,c,a}$. Applying to that matrix formula:

$$\Delta z_{b,c} = \text{median}(\Delta z_{b,c,a})$$

gives in return a two dimensional matrix corresponding to B-scans (dimension b) and layers (dimension c). Every column of that matrix is subjected to second median operation:

$$\Delta z_b = \text{median}(\Delta z_{b,c})$$

Thus a vector of offsets $\Delta z_b$ corresponding to all B-scans is obtained.

An interesting alternative is use the offsets matrix $\Delta z_{b,c,a}$ to correct particular A-scans without generalization to B-scan.

Although STEP15a applies quadratic regression, in general, it is possible to model the values as an nth order polynomial, yielding the general polynomial regression model:

$$z = a_0 + a_1 y + a_2 y^2 + a_3 y^3 + \ldots + a_m y^m + \varepsilon$$

Conveniently, these models are all linear from the point of view of estimation, since the regression function is linear in terms of the unknown parameters $a_0, a_1, \ldots$. Therefore, for least squares analysis, the computational and inferential problems of polynomial regression can be completely addressed using the techniques of multiple regression. This is done by treating $y, y^2, \ldots$ as being distinct independent variables in a multiple regression model.

Also, polynomial regression is just one example of regression analysis using basis functions to model a functional relationship between two quantities. A drawback of polynomial bases is that the basis functions are "non-local", meaning that the fitted value of z at a given value $y=y_0$ depends strongly on data values with y far from $y_0$. As is well known in the field of modern statistics, polynomial basis-functions can be used along with new basis functions, such as splines, radial basis functions, and wavelets. These families of basis functions offer a better fit for many types of data.

The goal of polynomial regression is to model a non-linear relationship between the independent and dependent variables (technically, between the independent variable and the conditional mean of the dependent variable). This is similar to the goal of nonparametric regression, which aims to capture non-linear regression relationships. Therefore, nonparametric regression approaches such as smoothing can be useful alternatives to polynomial regression. Some of these methods make use of a localized form of classical polynomial regression. An advantage of traditional polynomial regression is that the inferential framework of multiple regression can be used (this also holds when using other families of basis functions such as splines).

The method can also be applied to perform two subsequent corrections along both axes x and z corresponding to plane X-Z in which B-scans are located. In such situation firstly the method is applied to the x-direction and secondly to the z-direction.

Although the embodiments presented above refer to OCT imaging of an eye persons skilled in the art will easily recognize that the invention is also applicable to other objects of well defined shape and layered structure of example a finger is good example of such object.

It will be appreciated that methods embodying the present invention may be computer-implemented methods. Thus, the present invention extends to a program which, when executed by a computer or processor, causes the computer or processor to carry out any of the methods described hereinbefore.

Such a program may be provided by itself or may be carried in, by or on a carrier medium. The carrier medium may be a storage medium or recording medium, in particular a computer-readable storage medium. Examples include a hard disk drive, DVD, or memory device.

The carrier medium may also be a transmission medium such as a signal. Thus, a program embodying the present invention may be distributed, downloaded or uploaded in the form of a signal through a network including the Internet. The program may be non-transitory.

Although various embodiments that incorporate the teachings of the present invention have been shown, those skilled in the art can readily devise many other varied embodiments that still incorporate these teachings.

The invention claimed is:

1. A method for geometric correction of tomograms obtained by means of optical coherence tomography imaging of a sample, the method comprising:
   obtaining a plurality of tomograms by means of optical coherence tomography imaging of the sample;
   obtaining a reference tomogram;
   for each of one or more tomograms to be corrected from among the obtained tomograms:
      (i) comparing the tomogram to be corrected with the reference tomogram to determine a relative geometric transformation of the tomogram to be corrected with respect to the reference tomogram, and
      (ii) generating a corrected scan by performing on the tomogram to be corrected a transform that relates to the determined relative geometric transformation,
   wherein the tomogram is a B-scan and generating a corrected tomogram involves calculating for the tomogram to be corrected a single offset value $\Delta z_b$ from a set of displacement values, and applying to the scan to be corrected a displacement equal to or derived from the single offset value $\Delta z_b$,
   wherein the step of comparing the tomogram to be corrected with the reference tomogram to determine a relative geometric transformation further comprises the step of calculating a set of displacements between a B-scan to be corrected b and a reference B-scan y by the formula:

$$\Delta z_{b,c,a} = z_{b,c,a} - z_{y,c,a}$$

Where
b denotes a B-scan index within a 3D data volume,
a denotes an index of A-scans within a single B-scan,
c denotes an index of the boundary for which the displacement is calculated,
$z_{b,c,a}$ is a position along a z-axis of a c-th boundary for an a-th A-scan of a b-th B-scan, and
$z_{y,c,a}$ is a position along the z-axis of c-th boundary for a-th A-scan of the reference B-scan, and
   wherein said single offset value $\Delta z_b$ is calculated by applying formulae:

$$\Delta z_{b,c} = \text{median}(\Delta z_{b,c,a}) \text{ or } \text{Average}(\Delta z_{b,c,a})$$

and $$\Delta z_b = \text{median}(\Delta z_{b,c}) \text{ or } \text{Average}(\Delta z_{b,c,a}).$$

2. A method as claimed in claim 1, wherein a vector of displacement values $\{\Delta z_a\}$ for each A-scan by A-scan compensating of a displacement of said B-scan.

3. A method according to claim 1, further comprising determining a curve fitting value based on the single offset value $\Delta z_b$, wherein the corrected tomogram is generated by performing on the tomogram to be corrected a transform that relates to the single offset value $\Delta z_b$ and the curve fitting value.

4. A method according to claim 3, wherein said curved fitting value is determined by applying a quadratic regression or polynomial regression to be the single offset value $\Delta z_b$.

5. A method as claimed in claim 1, wherein the sample is a fundus.

6. A method according to claim 1, wherein the relative geometric transformation includes displacement.

7. A method as claimed in claim 1, wherein the reference tomogram is an obtained tomogram other than the tomogram to be corrected.

8. A method as claimed in claim 7, wherein the reference tomogram and the tomogram to be corrected are adjacent tomograms.

9. A method as claimed in claim 7, comprising performing a series of iterations, each of said iteration having such a tomogram to be corrected and such a reference tomogram and serving to determine a relative geometric transformation of the tomogram to be corrected with respect to the reference tomogram, and the reference tomogram of a current iteration being the tomogram to be corrected of the precedent iteration.

10. A method as claimed in claim 9, comprising selecting the reference tomogram from among a set of available tomogram.

11. A method as claimed in claim 10, wherein reference tomogram is a center tomogram among the set of available tomograms, the available tomograms being collected along a predetermined axis.

12. A device for geometric correction of tomograms obtained by means of optical coherence tomography imaging of a sample, the apparatus comprising:
an obtainer that obtains a plurality of tomograms by means of optical coherence tomography imaging of the sample;
a reference tomogram obtainer that obtains a reference tomogram;
a generator that, for each one or more tomograms to be corrected from among the obtained tomograms:
(i) compares the tomograms to be corrected with the reference tomogram to determine a relative geometric transformation of the tomogram to be corrected with respect to the reference tomogram, and
(ii) generates a corrected scan by performing on the tomogram to be corrected a transform that relates to the determined relative geometric transformation,
wherein the tomogram is a B-scan and generating a corrected tomogram involves calculating for the tomogram to be corrected a single offset value $\Delta z_b$ from a set of displacement values, and applying to the scan to be corrected a displacement equal to or derived from the single offset value $\Delta z_b$,
wherein the step of comparing the tomogram to be corrected with the reference tomogram to determine a relative geometric transformation further comprises the step of calculating a set of displacements between a B-scan to be corrected b and a reference B-scan y by the formula:

$$\Delta z_{b,c,a} = z_{b,c,a} - z_{y,c,a}$$

where
b denotes a B-scan index within a 3D data volume,
a denotes an index of A-scans within a single B-scan,
c denotes an index of the boundary for which the displacement is calculated,
$z_{b,c,a}$ is a position along a z-axis of a c-th boundary for an a-th A-scan of a b-th B-scan, and
$z_{r,c,a}$ is a position along the z-axis of a c-th boundary for an a-th A-scan of the reference B-scan, and
wherein said single offset value $\Delta z_b$ is calculated by applying formulae:

$$\Delta z_{b,c} = \text{median}(\Delta z_{b,c,a}) \text{ or Average}(\Delta z_{b,c,a}), \text{ and}$$

$$\Delta z_b = \text{median}(\Delta z_{b,c}) \text{ or Average}(\Delta zb,c).$$

13. A non-transitory computer-readable carrier medium comprising processor executable code which upon execution by one or more processors cause the one or more processors to perform a method for geometric correction of tomograms obtained by means of optical coherence tomography imaging of a sample, the method comprising:
an obtainer that obtains a plurality of tomograms by means of optical coherence tomography imaging of the sample;
a reference tomogram obtainer that obtains a reference tomogram;
a generator that, for each one or more tomograms to be corrected from among the obtained tomograms:
(i) compares the tomograms to be corrected with the reference tomogram to determine a relative geometric transformation of the tomogram to be corrected with respect to the reference tomogram, and
(ii) generates a corrected scan by performing on the tomogram to be corrected a transform that relates to the determined relative geometric transformation,
wherein the tomogram is a B-scan and generating a corrected tomogram involves calculating for the tomogram to be corrected a single offset value $\Delta z_b$ from a set of displacement values, and applying to the scan to be corrected a displacement equal to or derived from the single offset value $\Delta z_b$,
wherein the step of comparing the tomogram to be corrected with the reference tomogram to determine a relative geometric transformation further comprises the step of calculating a set of displacements between a B-scan to be corrected b and a reference B-scan y by the formula:

$$\Delta z_{b,c,a} = z_{b,c,a} - z_{y,c,a}$$

where
b denotes a B-scan index within a 3D data volume,
a denotes an index of A-scans within a single B-scan,
c denotes an index of the boundary for which the displacement is calculated,
$z_{b,c,a}$ is a position along a z-axis of a c-th boundary for an a-th A-scan of a b-th B-scan, and
$z_{r,c,a}$ is a position along the z-axis of a c-th boundary for an a-th A-scan of the reference B-scan, and
wherein said single offset value $\Delta z_b$ is calculated by applying formulae:

$$\Delta z_{b,c} = \text{median}(\Delta z_{b,c,a}) \text{ or Average}(\Delta z_{b,c,a}), \text{ and}$$

$$\Delta z_b = \text{median}(\Delta z_{b,c}) \text{ or Average}(\Delta zb,c).$$

* * * * *